US006919197B2

(12) United States Patent
Gerber et al.

(10) Patent No.: US 6,919,197 B2
(45) Date of Patent: Jul. 19, 2005

(54) MATERIALS AND METHODS FOR THE EFFICIENT PRODUCTION OF *PASTEURIA*

(75) Inventors: John F. Gerber, Gainesville, FL (US); James H. White, Gainesville, FL (US)

(73) Assignee: Entomos, Inc., Gainesville, FL (US)

( * ) Notice: Subject to any disclaimer, the term of this patent is extended or adjusted under 35 U.S.C. 154(b) by 2 days.

(21) Appl. No.: 10/761,509

(22) Filed: Jan. 20, 2004

(65) Prior Publication Data

US 2004/0137600 A1 Jul. 15, 2004

Related U.S. Application Data

(63) Continuation of application No. 09/636,185, filed on Aug. 10, 2000, now abandoned.
(60) Provisional application No. 60/148,154, filed on Aug. 10, 1999.

(51) Int. Cl.$^7$ .............................. C12N 1/20; C12N 1/00
(52) U.S. Cl. ................... 435/252.1; 435/243; 435/244; 435/253.6
(58) Field of Search ................................ 435/243, 244, 435/252.1, 253.6

(56) References Cited

U.S. PATENT DOCUMENTS 5,094,954 A 3/1992 Previc et al.

FOREIGN PATENT DOCUMENTS

| JP | 06165670 A | 6/1994 |
|---|---|---|
| JP | 06165670 A | 6/1994 |
| WO | WO 99/05325 | 2/1999 |

OTHER PUBLICATIONS

Dabire, K.R. et al. "Indirect effects of the bacterial soil aggregation on the distribution of *Pasteuria penetrans*, an obligate bacterial parasite of plant–parasitic nematodes," *Geoderma* (2001), vol. 102, pp. 139–152.

Duponnois, R. et al. "Effect of the rhizosphere microflora on *Pasteuria Penetrans* Parasitizing *Meloidogyne Graminocola*," *Nematol. Medit.* (1997), vol. 25, pp. 99–103.

ATCC: ( 1992) *Bacteria & Bacteriophages*, 18$^{th}$ Ed., pp. 478–479.

Bishop, A.H. and D.J. Ellar (1991) "Attempts to Culture *Pasteuria penetrans* in vitro." *Biocontrol Science and Technology*. vol. 1, pp. 101–114.

Brock, T. et al. (1991) *Biology of Microorganisms*. Simon & Schuster, Englewood Cliffs, NJ; 6$^{th}$ Ed. pp. 474–483.

Chen and Dickson (1998) "Review of *Pasteuria penetrans*: Biology, ecology and biological control potential." *J. Nematology*, vol. 30, pp. 313–340.

Duponnois, R. et al. (1999) "Beneficial effects of *Enterobacter cloacae* and *Pseudomonas mendocina* for biocontrol of *Meloidogyne incognita* with the endospore–forming bacterium *Pasteuria penetrans*,"*Nematology*, vol. 1, No. 1, pp. 95–101.

Duponnois, R. and A.M. BA (1998) "Influence of the Microbial Community of a Sahel Soil on the Interactions Between *Meloidogyne Javanica* and *Pasteuria Penetrans*." *Int. J. Nematol. Res.* vol. 44, pp. 331–344.

Fire, A. et al. (1998) "Potent and specific genetic interference by double–stranded RNA in *Caenorhabditis elegans.*" *Nature*. vol. 391, pp. 806–811.

Reise, R.W. et al. (1998) Abstracts of the 27$^{th}$ Annual Meeting Society of Nematologists, p. 75.

Reise, R.W. et al. (1991) "Limited In–vitro Cultivation of Pasteuria–Nishizawe." *Journal of Nematology*, vol. 23, No. 4, pp. 547–548, abstract.

Verdeho, S. and R. Mankau (1986) *Journal of Nematology*. vol. 18, p. 635.

Primary Examiner—Patricia Leith
(74) Attorney, Agent, or Firm—Saliwanchik, Lloyd & Saliwanchik

(57) ABSTRACT

The subject invention provides novel and advantageous methods for growing bacteria. The methods of the subject invention are particularly advantageous for growing parasitic bacteria, in vitro, without the presence of host tissue. In one embodiment of the subject invention, *Pasteuria* spores, such as those that infect the rootknot nematode *Meloidogyne arenaria* or other host nematodes, are grown in vitro. The process of the subject invention is highly advantageous because *Pasteuria* can be grown in the absence of nematode tissue.

3 Claims, No Drawings

MATERIALS AND METHODS FOR THE EFFICIENT PRODUCTION OF *PASTEURIA*

CROSS-REFERENCE TO RELATED APPLICATION

This application is a continuation of U.S. application Ser. No. 09/636,185, filed Aug. 10, 2000 now abandoned; which claims the benefit of U.S. Provisional Application No. 60/148,154, filed Aug. 10, 1999.

BACKGROUND OF THE INVENTION

This invention relates to methods for the production of *Pasteuria*, or *Pasteuria*-like, bacteria. These bacteria are able to produce endospores that have the unique and useful property of being able to attach to, infect, grow in, re-sporulate in, and kill certain types of phytopathogenic nematodes and other soil-dwelling nematodes.

Crop losses due to phytopathogenic nematodes exact a heavy toll in US agriculture. For 1994, Koenning et al. (*Nematology* 31:587–618, 1999) estimate losses due to nematodes to be in excess of $1.5 billion for corn, soy, wheat, cotton, peanut and vegetable combined. These phytopathogenic nematodes come from the phylum *Nematoda*, within the orders *Tyienchida* and *Dorylamide*. Expenditures in the US for fumigants and nematicides on these and other crops totaled just over $400 million in 1996 (Chemical Economics Handbook, SRI International, 1997).

Phytopathogenic nematodes are particularly difficult to control because they are covered with a thick, impermeable cuticle, or outer covering, and have very few sensory neurons. Since many pest control compounds operate as neurotoxins, the low number of neurons exposed by phytopathogenic nematodes decreases the effective target area for nematicidal compounds and has resulted in the development of nematicidal compounds with exquisitely high neurotoxic properties. Furthermore, because the phytopathogenic nematodes are found in soil or plant roots, exposing the phytopathogenic nematodes to control agents also is difficult to achieve and puts the water table at risk of contamination from those toxic compounds. The use of nematicides based on neurotoxins has been demonstrated to contaminate both ground and surface water. Consequently, many of these compounds are being removed from the market for public health reasons.

Fumigation of soil prior to planting is a popular method for controlling nematodes. One of the most popular fumigants, methyl bromide, is slated for removal from use because of its ozone destroying properties. However, this practice of soil fumigation kills organisms in soil indiscriminately and runs the risk of eliminating beneficial microbes as well as disease organisms. The overall market for an effective nematicide with benign environment effects is estimated to approach one billion dollars on a world-wide basis.

*Pasteuria* was first described in 1888 by Mechnikoff (Annales de l'Institut Pasteur 2:165–170) as a parasite of water fleas. Subsequently, Cobb described a Pasteuria infection of the nematode *Dorylaimus bulfiferous* (2$^{nd}$ ed. Hawaiian Sugar Planters Assoc., Expt. Sta. Div. Path. Physiol. Bull. 5:163–195, 1906). In the intervening years, Pasteuria infections of virtually every known nematode have been observed, and their potential for use in biological control of phytopathogenic nematodes has been noted (Chen and Dickson [1998] *J. Nematology* 30:313–340).

Although bacteria of the Pasteuria group have a recognized potential for use as biorational control agents against phytopathogenic nematodes, their widespread use in commercial agriculture will depend on the availability of reliable methods for the large-scale production of bacteria having specificity against the phytopathogenic nematodes of concern to farmers.

Previous attempts at in vitro culture of *Pasteuria* used vegetative phase tissue recovered from infected females which were surface disinfected with materials such as "Clorox" and were cultured with antibiotics to avoid contamination. Rich media such as Graces Insect Media, Schneiders Insect Media, or Leibovitz Insect Media were used and supplemented with numerous materials, see (Bishop and Ellar).

Most of the experimental work with the Pasteuria group of bacteria has used spores produced in live nematodes, cultivated on whole plants in greenhouses where aseptic conditions do not prevail. In two exceptions, Verdeho et al. (Verdeho, S. and R. Mankau [1986] *Journal of Nematology* 18:635) have reported on the oligoxenic culture of *Pasteuria penetrans* in live *Meloidogyne incognita* on excised tomato root culture; and Reise et al. (Reise, R. W., K. J. Hackett, R. M. Sayre, and R. N. Huettel [1988] Abstracts of the 27$^{th}$ Annual Meeting Society of Nematologists, p. 75) have studied factors in various tissue culture media affecting *Pasteuria* isolates from *Heterodera glycines, Meloidogyne incognita*, and *Pratylenchus brachyurus*. Their attempts are directed at a genuine in vitro cultivation of *Pasteuria*, which attempts fail on the basis of the fundamental criterion that a genuine in vitro cultivation of any prokaryotic organism must be marked by a continual survival and proliferation of the organisms, upon transfer to a fresh medium, at some definable growth rate that is characteristic of the genotype of the organism and the environmental conditions.

U.S. Pat. No. 5,094,954 describes an alternative method for producing endospores from *Pasteuria* by growing the bacteria on explanted nematode tissue. In the method of U.S. Pat. No. 5,094,954, the nematode tissue may be prepared, for example, by decapitating and decaudating nematodes, or by osmotic and/or enzymatic disruption of the nematode cuticle. The nematode tissue is explanted onto media which is designed to nourish the tissue and keep it in a metabolically active state. The tissue is then induced into growth and cell proliferation. Thus, this method does not rely on in vitro cultivation of the *Pasteuria*, but is directed at the production of *Pasteuria* spores on explanted or cultured nematode tissue.

Thus, although *Pasteuria* was first reported as far back as 1888, all attempts to culture the microbe in vitro have failed to produce a viable means of producing endospores. Therefore, there remains in this art a great need for a method of producing *Pasteuria* by spore formation following true in vitro growth of the vegetative phase of *Pasteuria* on an artificial growth medium consisting of inexpensive, readily available materials. Such systems are not known at this time.

BRIEF SUMMARY OF THE INVENTION

The subject invention provides novel and advantageous methods for growing bacteria. The methods of the subject invention are particularly advantageous for growing parasitic bacteria, in vitro, without the presence of host tissue. In one embodiment of the subject invention, *Pasteuria* spores, such as those that infect the rootknot nematode *Meloidogyne arenaria* or other host nematodes, are grown in vitro. The process of the subject invention is highly advantageous because *Pasteuria* can be grown in the absence of nematode tissue.

The bacteria spores obtained using the methods of the subject invention can then be used in any appropriate composition or process. This greatly simplifies the process and reduces material and labor costs. Specifically exemplified herein is the production of Pasteuria endospores and the use of these spores in nematode control programs.

In a specific embodiment of the subject invention, the growth of *Pasteuria* is carried out on agar plates or in liquid. Also, preferably, no antibiotic or bleach is added to the growth medium.

Advantageously, the method of the subject invention results in growth of bacterial mass and an increase in the number of cellular units of the vegetative stage of the bacteria. Subsequently, sporulation occurs from the late vegetative phase of the bacteria with production of mature, dormant spores. In the case of *Pasteuria*, the spores are infective for nematodes, including *Meloidogyne arenaria* and other nematode species.

A further aspect of the subject invention concerns the identification of helper factor(s) which, when present in *Pasteuria* growth medium, facilitate the in vitro growth of the *Pasteuria*. In one embodiment, the helper factor is a microorganism. A specific isolate of this helper factor has been deposited with the American Type Culture Collection and has been assigned the deposit number ATCC PTA-2324. In a further embodiment, the helper factor is a chemical compound which, when present in the *Pasteuria* growth medium, facilitates the in vitro growth of Pasteuria. Specifically exemplified herein is the helper factor designated HF-1 which can be obtained from the culture designated ATCCPTA-2324.

Further aspects of the subject invention include compositions comprising Pasteuria endospores and the use of these compositions to control phytopathogenic nematodes.

Another aspect of the subject invention pertains to the use of the helper factors described herein to promote the growth of *Pasteuria* in or around plants thereby controlling nematodes.

BRIEF DESCRIPTION OF THE SEQUENCE

SEQ ID NO. 1 shows a polynucleotide sequence of a helper factor bacteria according to the subject invention.

DETAILED DISCLOSURE OF THE INVENTION

The subject invention provides methods for the efficient production of bacterial spores. Specifically exemplified herein is the in vitro production of *Pasteuria* endospores. In accordance with the subject invention, *Pasteuria* are grown and produce endospores that have the unique and useful property of being able to attach to, infect, grow in, re-sporulate in, reduce the fecundity of, and/or kill certain types of phytopathogenic nematodes and other soil-dwelling nematodes. In addition, *Pasteuria* can reduce the ability of nematodes to infect plants.

In one aspect, the subject invention provides a method for producing endospores of parasitic bacteria species in vitro without the presence of living host tissue. These parasitic bacteria include, for example, various bacillus species. In a preferred embodiment, a *Pasteuria* production process of the subject invention involves the use of a helper factor such as, for example, a second bacterium or a chemical factor produced by a second bacterium. This method is highly advantageous because it requires only simple growth media which is, preferably, not stirred or mixed and has no antibiotics added. No nematode tissue is needed.

In a further aspect, the subject invention provides a method for protecting plants from plant pathogenic nematodes. This method can comprise modifying a plant so that it produces a helper factor.

In a further aspect, the subject invention provides a method for preventing or controlling plant pathogenic nematodes by the application to the plant, or the plant's surroundings, a helper factor which facilitates *Pasteuria* growth and/or colonization.

In a preferred embodiment, the subject invention provides a novel method for growing *Pasteuria* bacteria for the production of spores which can then be used as a biocontrol agent for nematodes. In particular, the novel procedure involves the in vitro growth of *Pasteuria*.

In a specific embodiment, the method of the subject invention involves growing *Pasteuria* on a nutrient broth (NB). In a preferred embodiment, the *Pasteuria* are grown in the absence of antibiotics and without stirring. Optionally, the NB may be supplemented with bovine calf serum (BCS) and/or an egg yolk preparation.

In a specific embodiment of the process of the subject invention, infected female nematodes are washed with water to remove attached debris, soil, microorganisms, etc. Preferably, the washing takes place without disinfectants or antibiotics. The nematodes are then crushed with, for example, slide cover slips which have been sterilized. A small amount of distilled water can be utilized to facilitate the crushing process. Once the crushed nematodes are prepared, they are then introduced into a nutrient medium and grown. This growth can be carried out at room temperature. A standard nutrient broth, optionally supplemented with bovine calf serum, can be utilized. The nutrient broth may also be supplemented with an egg yolk preparation, peanut oil, or other source of lipids. The preparation is permitted to grow, preferably without stirring, at room temperature. Within a period of several hours up to several days, swimming rod-shaped organisms will appear. Production of spores can then be induced as described herein.

In one embodiment of the process of the subject invention, after appearance of motile rods, the preparation can be transferred to a solid growth medium in, for example, a petri dish. Typically, within about 24 hours of growth in the nutrient medium, colonies will appear on the plates (petri dishes). The colonies which appear on the petri dishes comprise the motile rod organisms first observed in the initial growth on nutrient medium. After appearance of the colonies in the nutrient medium, induction of spore formation can be done by, for example, adding manganese sulfate and/or lipids.

In a preferred embodiment of the subject invention, the growth process is carried out to completion in liquid growth medium. This process is simple and highly efficient.

If desired, the helper microorganisms of the subject invention can be separated from the growing *Pasteuria* by a membrane which allows the passage of a chemical helper factor but which blocks the passage of entire microbes. In a specific embodiment, membranes having a pore size of about 0.5 μm can be used to separate the *Pasteuria* from the helper microbes while permitting the passage of the chemical helper factor. In a more specific embodiment the pore size is 0.45 μm.

Spores will typically form within about 24 hours of spore induction. These spores have been determined to be capable of attaching to J2 juvenile nematodes.

Although not wishing to be bound by theory, it appears that the growth system of the subject invention involves multiple organisms. Thus, for example, the motile rods observed in the nutrient growth media facilitate the optimal growth of the *Pasteuria*. For convenience, reference herein to "helper factor" refers to the motile rods, other microbes, or factors produced by the motile rods or other microbes, which facilitate or enhance the growth of *Pasteuria*. The helper factor(s) are believed to exist internal in the nematodes, or their host plant, and are made available to perform their functions in the system of the subject invention when nematodes are, for example, crushed.

Thus, one aspect of the subject invention is an efficient system for the in vitro production of *Pasteuria*. In a preferred embodiment, this system utilizes helper factor(s) to achieve optimal production of *Pasteuria*.

A further aspect of the subject invention pertains to the manipulation of the helper factor(s) of the subject invention to effect control of plant parasitic nematodes. This aspect of the subject invention relates to the involvement of the helper factors in the nematodes' infection of plants. By interfering with the ability of the helper factor to modulate and/or facilitate infection of plants by nematodes it is possible to prevent or inhibit nematode infection of plants. This interference with this function of the helper factor(s) can be achieved by, for example, exposing the helper factors to antibiotics or other agents (such as antisense DNA or RNAi) which inhibit the ability of the helper factor(s) to promote nematode infection (Fire, A., S. Xu, M. K. Montgomery, S. A. Kostas, S. E. Driver, and C. C. Mello. [1998] "Potent and specific genetic interference by double-stranded RNA in *Caenorhabditis elegans*" Nature 391:806–811). Preferably, the inhibiting substance would be present in the roots of the plant.

A further aspect of the subject invention is the use of helper factor(s) to promote efficient colonization and/or infectivity by *Pasteuria*. Thus, live microbial helper factors such as the motile rods exemplified herein can be applied to the situs of plants to promote the colonization by indigenous *Pasteuria*. Alternatively, microbial helper factors can be mixed with *Pasteuria* and applied to the situs of plants. In a further embodiment, a chemical helper factor, such as HF-1 can be applied with or without contemporaneous application of *Pasteuria*. Helper factors may be applied at the time of planting, either as a seed coat or as a separate composition. Plants may also be transformed to express a chemical helper factor. In a preferred embodiment the helper factor would be expressed in plant roots.

A further aspect of the subject invention pertains to the motile rod organisms which are associated with the ability of the *Pasteuria* to grow in vitro. A culture of the microbes has been deposited with the American Type Culture Collection (ATCC), 10801 University Blvd., Manassas, Va. 20110–2209 USA. The deposit has been assigned accession number ATCC No. PTA-2324 by the repository and was deposited on Aug. 2, 2000.

The subject deposit was deposited under conditions that assure that access to the deposit will be available during the pendency of this patent application to one determined by the Commissioner of Patents and Trademarks to be entitled thereto under 37 CFR 1.14 and 35 U.S.C. 122. The deposit will be available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least thirty (30) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

A further aspect of the subject invention pertains to a helper factor of the subject invention designated HF-1. HF-1 is produced by the motile rod isolate described herein and has a size of less than about 0.50 $\mu$m. This factor is particularly advantageous because it is associated with the ability of *Pasteuria* to grow in vitro.

Following are examples which illustrate procedures for practicing the invention. These examples should not be construed as limiting. All percentages are by weight and all solvent mixture proportions are by volume unless otherwise noted.

EXAMPLE 1

Preparation of Nematodes and Growth of Pasteuria

Infected Rootknot (*Meliodogyne arenaria*) females were surface washed in autoclaved water. Approximated 100 ml of water were passed over the nematodes in a fine mesh screen. These nematodes were then crushed between autoclaved glass slides in a drop of water. The suspension of material was inoculated into 24 well, sterile plates which contained sterile insect cell culture media (0.5% glucose and Leibovitz) with 5% Bovine Calf Serum (BSC) added. Growth was observed within 24 hours at room temperature. The growth consisted of motile rods, which was not expected. This material was observed for several days and a few refractile bodies resembling *Pasteuria* endospores appeared. When stained with Gram's Stain the culture contained both negative and positive material. The endospore-like bodies were Gram positive.

Material from agar plates was inoculated into nutrient broth (NB) with BCS. Within 24 hours abundant growth was evident including structures which appeared to be identical to structures found in infected nematodes. In several days refractile bodies filled these structures.

EXAMPLE 2

Choice of Medium

NB and 0.5% glucose were the preferred media. Spores produced in the NB attached more readily to the J2's than those produced in 0.5% glucose. A sterile egg yolk preparation was added to the NB and, within 24 hours, profuse endospores were produced. This media contained 5% BCS and 5% egg yolk mixture. The spores attached very readily to the J2's. Subsequently, a saturated solution of Wesson's salts were added to the NB and the BCS was eliminated. Again abundant spores were obtained within 24 hours.

The NB media containing the egg yolk and salts was diluted 1:1, 1:5 and 1:10. In all cases growth and spores were obtained. One percent glucose was used with the egg yolk and salts and good growth and spores were obtained within 24 hours.

Subsequently it was determined that the egg yolk mixture could be reduced and that dried egg yolk could be used. The most recent media is either NB (8 g/l) or Glucose (10 g/l) plus 2.5% egg yolk and 5% saturated Wesson Salts. The richness of these media can be reduced if desired.

EXAMPLE 3

Primary Culture Isolation

*Pasteuria*-infected nematodes were harvested from tomato roots 12 to 15 days after inoculating the plants. The nematodes were surface sterilized in 10% Chlorox solution for 5 minutes. From this point aseptic techniques were strictly enforced. Infected nematodes were rinsed twice in 0.6% saline solution. After the final rinse the individual nematodes were placed in wells containing 1 ml Nutrient Broth in a 24-well plate. Using sterile toothpicks, nematodes were crushed to release the vegetative structures of *Pasteuria*. All cultures were incubated at 30° C. The presence of these structures was confirmed using an inverted microscope (400×). Cultures were monitored on a daily basis for the presence of mycelial balls, MB, (vegetative stage of *Pasteuria* growth). Helper factors (contained in 0.45 micron membrane tissue culture inserts) was introduced to some of the cultures 24 hours after initial incubation.

The number and quality of the MB determined the progress in each step. In wells which received no insert, the number of MB and the degree of refractivity decreased as the cultures got older. Almost no MB were present after one week. In the wells which received the helper factor (inserts) for a total of three days, the number of MB increased and the degree of their refractivity remained the same for about 13 days. At this point the MB morphology changed and their edges became rough. They disappeared from the wells after 15 days. At day 16 mature spores were detected.

EXAMPLE 4

Attachment of *Pasteuria* Spores to Nematodes

Spores harvested from the media described in Example 2 were used for attachment trials on J2 Root knot nematodes using the method described by Dickson. Approximately 1 ml of a suspension containing J2 nematodes was placed in a 1.5 ml centrifuge tube and one drop of the suspension containing the refractile bodies was added. The tubes were spun at 9000 rpm for 3 minutes and the material placed in a well and observed with an inverted microscope. There was clear indication that the refractive bodies were attached to the J2.

In another experiment, J2's were briefly surface sterilized and then placed in DI water. Spores were then added to the J2's in the wells and attached without centrifugation. Several wells containing J2's with spores attached were observed to determine if the attachments were stable. The wells were examined every day for 10 days and all the attachments were stable. During these observations it was evident that the nematodes would burrow into clumps of matrix material and that the motile rods were still active, even though the only media available was that which was contained in the one drop of spore inoculumn added to the 1.5 ml suspension of J2's. After about 14 days, some of the J2's began to molt and after a few more days all of the J2's began to molt.

There were several differences with the in vitro produced refractile bodies and in vivo endospores. The in vivo material tended to be very dense concentrations of endospores and included abundant vegetative material mixed with the spores so that a clump of endospores appeared to be attached to the J2's rather than a single spore. However, on closer examination it appeared that one or two spores were attached and the rest were still in the vegetative matrix and were not directly attached to the J2's. Another difference was that, under some circumstances, the in vitro endospores appeared slightly smaller.

EXAMPLE 5

Field Trials

Several thousand *M. arenaria* J2 nematodes with refractile bodies attached were added to nematode free tomatoes growing in pasteurized soils. After 25 to 30 days the roots were harvested and examined. Female Rootknot nematodes infected with *Pasteuria* and filled with endospores were recovered.

The tomato experiment was repeated and in all cases female root knot nematodes were recovered which were filled with *Pasteuria* penetrans endospores.

EXAMPLE 6

Identification of Helper Factor(s)

Nutrient broth was inoculated with material from nutrient agar, which had undergone numerous passages. In all cases refractile bodies were observed within a few days. Nucleotide sequence data was obtained from in vitro endospores. When compared with sequences of DNA on deposit at GenBank, it was clear that the motile rods were not *Pasteuria* and that there must be two organisms present.

A polynucleotide sequence obtained from a motile rod helper factor of the subject invention is shown in SEQ ID NO. 1.

The DNA from the motile rods has 98% homology with *Enterobacter cloacae* and *Pantoea* ssp., as well as others.

The helper factors of the subject invention include microbes having high sequence similarity to SEQ. ID NO. 1. This high sequence similarity would typically be greater than 50% over a span of at least about 20 bases, preferably greater than 80% and most preferably greater than 90%. Such helper factor microbes can be readily identified by, for example, using SEQ. ID. NO. 1, or fragments thereof, as DNA probes.

EXAMPLE 7

Polynucleotide Probes and Primers

DNA possesses a fundamental property called base complementarity. In nature, DNA ordinarily exists in the form of pairs of anti-parallel strands, the bases on each strand projecting from that strand toward the opposite strand. The base adenine (A) on one strand will always be opposed to the base thymine (T) on the other strand, and the base guanine (G) will be opposed to the base cytosine (C). The bases are held in apposition by their ability to hydrogen bond in this specific way. Though each individual bond is relatively weak, the net effect of many adjacent hydrogen bonded bases, together with base stacking effects, is a stable joining of the two complementary strands. These bonds can be broken by treatments such as high pH or high temperature, and these conditions result in the dissociation, or "denaturation," of the two strands. If the DNA is then placed in conditions which make hydrogen bonding of the bases thermodynamically favorable, the DNA strands will anneal, or "hybridize," and reform the original double-stranded DNA. If carried out under appropriate conditions, this hybridization can be highly specific. That is, only strands with a high degree of base complementarity will be able to form stable double-stranded structures. The relationship of the specificity of hybridization to reaction conditions is well known. Thus, hybridization may be used to test whether two pieces of DNA are complementary in their base sequences. It is this hybridization mechanism which facilitates the use of probes of the subject invention to readily detect and characterize DNA sequences of interest.

The specifically exemplified polynucleotides of the subject invention can themselves be used as probes. Additional polynucleotide sequences can be added to the ends of (or internally in) the exemplified polynucleotide sequences so that polynucleotides that are longer than the exemplified polynucleotides can also be used as probes. Thus, isolated polynucleotides comprising one or more of the exemplified sequences are within the scope of the subject invention. Polynucleotides that have less nucleotides than the exemplified polynucleotides can also be used and are contemplated within the scope of the present invention. For example, for some purposes, it might be useful to use a conserved sequence from an exemplified polynucleotide wherein the conserved sequence comprises a portion of an exemplified sequence. Thus, polynucleotides of the subject invention can be used to find additional, homologous (wholly or partially) genes and microbes.

Probes of the subject invention may be composed of DNA, RNA, or PNA (peptide nucleic acid). The probe will normally have at least about 10 bases, more usually at least about 17 bases, and may have about 100 bases or more. Longer probes can readily be utilized, and such probes can be, for example, several kilobases in length. The probe need not have perfect complementarity to the sequence to which it hybridizes. The probes may be labeled utilizing techniques that are well known to those skilled in this art.

One approach for the use of the subject invention as probes entails first identifying DNA segments that are homologous with the disclosed nucleotide sequences using, for example, Southern blot analysis of a gene bank.

One hybridization procedure useful according to the subject invention typically includes the initial steps of isolating the DNA sample of interest and purifying it chemically. Either lysed nematodes (or other parasite hosts, or other samples) or total fractionated nucleic acid isolated from nematodes can be used. Cells can be treated using known techniques to liberate their DNA (and/or RNA). The DNA sample can be cut into pieces with an appropriate restriction enzyme. The pieces can be separated by size through electrophoresis in a gel, usually agarose or acrylamide. The pieces of interest can be transferred to an immobilizing membrane.

The particular hybridization technique is not essential to the subject invention. As improvements are made in hybridization techniques, they can be readily applied. The probe and sample can then be combined in a hybridization buffer solution and held at an appropriate temperature until annealing occurs. Thereafter, the membrane is washed free of extraneous materials, leaving the sample and bound probe molecules typically detected and quantified by autoradiography and/or liquid scintillation counting. As is well known in the art, if the probe molecule and nucleic acid sample hybridize by forming a strong non-covalent bond between the two molecules, it can be reasonably assumed that the probe and sample are essentially identical or very similar.

The probe's detectable label provides a means for determining in a known manner whether hybridization has occurred.

In the use of the nucleotide segments as probes, the particular probe is labeled with any suitable label known to those skilled in the art, including radioactive and non-radioactive labels. Typical radioactive labels include $^{32}P$, $^{35}S$, or the like. Non-radioactive labels include, for example, ligands such as biotin or thyroxine, as well as enzymes such as hydrolases or peroxidases, or the various chemiluminescers such as luciferin, or fluorescent compounds like fluorescein and its derivatives. In addition, the probes can be made inherently fluorescent as described in International Application No. WO 93/16094. Various degrees of stringency of hybridization can be employed. The more stringent the conditions, the greater the complementarity that is required for duplex formation. Stringency can be controlled by temperature, probe concentration, probe length, ionic strength, time, and the like. Preferably, hybridization is conducted under moderate to high stringency conditions by techniques well known in the art, as described, for example, in Keller, G. H., M. M. Manak (1987) *DNA Probes*, Stockton Press, New York, N.Y., pp. 169–170.

As used herein "moderate to high stringency" conditions for hybridization refers to conditions that achieve the same, or about the same, degree of specificity of hybridization as the conditions "as described herein." Examples of moderate to high stringency conditions are provided herein. Specifically, hybridization of immobilized DNA on Southern blots with $^{32}P$-labeled gene-specific probes was performed using standard methods (Maniatis et al.). In general, hybridization and subsequent washes were carried out under moderate to high stringency conditions that allowed for detection of target sequences with homology to sequences exemplified herein. For double-stranded DNA gene probes, hybridization was carried out overnight at 20–25° C. below the melting temperature (Tm) of the DNA hybrid in 6×SSPE, 5× Denhardt's solution, 0.1% SDS, 0.1 mg/ml denatured DNA. The melting temperature is described by the following formula from Beltz et al. (1983):

$$Tm=81.5° C.+16.6 \text{ Log}[Na+]+0.41 \text{ (\% G+C)}-0.61 \text{ (\% formamide)}-600/\text{length of duplex in base pairs.}$$

Washes are typically carried out as follows:

(1) Twice at room temperature for 15 minutes in 1×SSPE, 0.1% SDS (low stringency wash).

(2) Once at Tm-20° C. for 15 minutes in 0.2×SSPE, 0.1% SDS (moderate stringency wash).

For oligonucleotide probes, hybridization was carried out overnight at 10–20° C. below the melting temperature (Tm) of the hybrid in 6×SSPE, 5× Denhardt's solution, 0.1% SDS, 0.1 mg/ml denatured DNA. Tm for oligonucleotide probes was determined by the following formula from Suggs et al. (1981):

$$Tm\ (° C.)=2(\text{number T/A base pairs})+4(\text{number G/C base pairs})$$

Washes were typically carried out as follows:

(1) Twice at room temperature for 15 minutes 1×SSPE, 0.1% SDS (low stringency wash).

(2) Once at the hybridization temperature for 15 minutes in 1×SSPE, 0.1% SDS (moderate stringency wash).

In general, salt and/or temperature can be altered to change stringency. With a labeled DNA fragment of greater than about 70 or so bases in length, the following conditions can be used:

| Low: | 1 or 2X SSPE, room temperature |
| --- | --- |
| Low: | 1 or 2X SSPE, 42° C. |
| Moderate: | 0.2X or 1X SSPE, 65° C. |
| High: | 0.1X SSPE, 65° C. |

Duplex formation and stability depend on substantial complementarity between the two strands of a hybrid, and, as noted above, a certain degree of mismatch can be tolerated. Therefore, polynucleotide sequences of the subject invention include mutations (both single and multiple), deletions, and insertions in the described sequences, and combinations thereof, wherein said mutations, insertions, and deletions permit formation of stable hybrids with a target polynucleotide of interest. Mutations, insertions, and deletions can be produced in a given polynucleotide sequence using standard methods known in the art. Other methods may become known in the future.

The mutational, insertional, and deletional variants of the polynucleotide sequences of the invention can be used in the same manner as the exemplified polynucleotide sequences so long as the variants have substantial sequence similarity with the original sequence. As used herein, substantial sequence similarity refers to the extent of nucleotide similarity that is sufficient to enable the variant polynucleotide to function in the same capacity as the original sequence. Preferably, this similarity is greater than 50%; more preferably, this similarity is greater than 75%; and most preferably, this similarity is greater than 90%. The degree of similarity needed for the variant to function in its intended capacity will depend upon the intended use of the sequence. It is well within the skill of a person trained in this art to make mutational, insertional, and deletional mutations that are designed to improve the function of the sequence or otherwise provide a methodological advantage.

In a further embodiment, the polynucleotide sequences of the subject invention (and portions thereof such as conserved regions and portions that serve to distinguish these sequences from previously-known sequences) can be used as, and/or used in the design of, primers for PCR amplification. In performing PCR amplification, a certain degree of mismatch can be tolerated between primer and template. Therefore, mutations, deletions, and insertions (especially additions of nucleotides to the 5' end) of the exemplified polynucleotides can be used in this manner. Mutations, insertions and deletions can be produced in a given primer by methods known to an ordinarily skilled artisan.

Other DNA sequences from the motile rod isolate exemplified herein can be used as the basis for DNA probes and/or primers to identify other helper factor microbes and genes.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A method for producing *Pasteuria* endospores in vitro, said method comprising introducing *Pasteuria* into a growth medium, growing the *Pasteuria* in said growth medium, and obtaining said endospores, wherein said growth medium comprises a microorganism having all the identifying characteristics of ATCC 2324.

2. The method, according to claim 1, wherein said growth medium does not comprise an antibiotic.

3. The method according to claim 1, wherein a compound selected from the group consisting of manganese sulfate and lipids is added to induce the production of endospores.

* * * * *

SEQUENCE LISTING

```
<160> NUMBER OF SEQ ID NOS: 1

<210> SEQ ID NO 1
<211> LENGTH: 1455
<212> TYPE: DNA
<213> ORGANISM: Unknown
<220> FEATURE:
<223> OTHER INFORMATION: Helper Factor  DNA is not Pasteuria but has 98%
      homology with Enterobacter cloacae and Pantoea ssp. and others.
<220> FEATURE:
<221> NAME/KEY: misc_feature
<222> LOCATION: (99)..(99)
<223> OTHER INFORMATION: n = a, c, g, or t.
<220> FEATURE:
<221> NAME/KEY: misc_feature
<222> LOCATION: (102)..(102)
<223> OTHER INFORMATION: n = a, c, g, or t.

<400> SEQUENCE: 1
ggcaggccta acacatgcaa tcgagcggca gcggaaagta gcttgctact ttgccggcga        60
gcggcggacg ggtgagtaat gtctgggaaa ctacctgang gntggggatc actactggaa       120
acagttgcta ataccgcata acgtctcaag accaaagagg gggaccttcg ggcctcttgc       180
catcagatgt gcccagatgg gattagctag taggtggggt aacggctcac ctaggcgacg       240
atccctagct ggtctgagag gatgaccagc cacactggaa ctgagacacg gtccagactc       300
ctacgggagg cagcagtggg gaatattgca caatgggcgc aagcctgatg cagccatgcc       360
gcgtgtatga agaaggcctt cgggttgtaa agtactttca gcggggagga aggcgttgag       420
gttaataacc tcagcgattg acgttacccg cagaagaagc accggctaac tccgtgccag       480
cagccgcggt aatacggagg gtgcaagcgt taatcggaat tactgggcgt aaagcgcacg       540
```

-continued

```
caggcggtct gtcaagtcgg atgtgaaatc cccgggctca acctgggaac tgcattcgaa      600
actggcaggc tagagtcttg tagagggggg tagaattcca ggtgtagcgg tgaaatgcgt      660
agagatctgg aggaataccg gtggcgaagg cggcccctg gacaaagact gacgctcagg       720
tgcgaaagcg tggggagcaa acaggattag atacctggt agtccacgcc gtaaacgatg       780
tcgacttgga ggttgtgccc ttgaggcgtg gcttccggag ctaacgcgtt aagtcgaccg      840 cctgggagt acggccgcaa ggttaaaact caaatgaatt gacgggggcc cgcacaagcg       900
gtggagcatg tggtttaatt cgatgcaacg cgaagaacct tacctactct tgacatccag      960
agaactttcc agagatggat tggtgccttc gggaactctg agacaggtgc tgcatggctg     1020
tcgtcagctc gtgttgtgaa atgttgggtt aagtcccgca acgagcgcaa cccttatcct     1080
ttgttgccag cggttaggcc gggaactcaa aggagactgc cagtgataaa ctggaggaag     1140
gtggggatga cgtcaagtca tcatggccct tacgagtagg gctacacacg tgctacaatg     1200
gcgcatacaa agagaagcga cctcgcgaga gcaagcggac ctcataaagt gcgtcgtagt     1260
ccggattgga gtctgcaact cgactccatg aagtcggaat cgctagtaat cgtagatcag     1320
aatgctacgg tgaatacgtt cccgggcctt gtacacaccg cccgtaaggg cgaattctgc     1380
agatatccat cacactggcg gccgctcgag cagcatctag agggcccaat tcgccctata     1440
gtgagtcgta ttaca                                                     1455
```